United States Patent [19]

Pindar et al.

[11] 4,273,891
[45] Jun. 16, 1981

[54] HYDROCARBON-SUBSTITUTED METHYLOL PHENOLS

[75] Inventors: John F. Pindar, Euclid; Jerome M. Cohen, University Heights; Charles P. Bryant, Euclid, all of Ohio

[73] Assignee: The Lubrizol Corporation, Wickliffe, Ohio

[21] Appl. No.: 830,931

[22] Filed: Sep. 6, 1977

Related U.S. Application Data

[63] Continuation-in-part of Ser. No. 613,664, Sep. 15, 1975, Pat. No. 4,053,428, which is a continuation-in-part of Ser. No. 540,470, Jan. 13, 1975, Pat. No. 3,980,569, which is a continuation-in-part of Ser. No. 451,644, Mar. 15, 1974, abandoned.

[51] Int. Cl.$^3$ ............... C08G 8/10; C08G 8/36; C08L 61/14; C10M 1/28
[52] U.S. Cl. ................. 525/145; 44/78; 252/52 A; 252/52 R; 528/152; 528/153; 528/159; 528/160; 568/611; 568/764
[58] Field of Search ........... 260/848; 528/153, 159, 528/160, 152; 568/764, 611; 252/52 R, 52 A; 44/78; 525/145

[56] References Cited

U.S. PATENT DOCUMENTS

| 2,163,637 | 6/1939 | Thomas | 260/848 |
|---|---|---|---|
| 2,707,715 | 5/1955 | Martin | 260/848 |
| 2,796,423 | 6/1957 | Cottle et al. | 260/410.9 |
| 2,912,395 | 11/1959 | Graham | 568/764 |
| 2,962,442 | 11/1960 | Andress | 252/51.5 |
| 3,127,251 | 3/1964 | DeGroote et al. | 44/66 |
| 3,211,804 | 10/1965 | Baum et al. | 260/848 |
| 3,306,938 | 2/1967 | Welch et al. | 568/764 |
| 3,336,226 | 8/1967 | Kantsky et al. | 252/42.7 |
| 3,501,527 | 3/1970 | Little et al. | 260/570.9 |
| 3,539,646 | 11/1970 | Dannels et al. | 528/152 |
| 3,637,430 | 1/1972 | Dahms et al. | 528/152 |
| 3,703,494 | 11/1972 | Anderson et al. | 528/152 |
| 3,737,465 | 6/1973 | Karll et al. | 260/619 A |
| 3,981,929 | 9/1976 | Davis et al. | 568/764 |
| 4,038,327 | 7/1977 | Brindell et al. | 568/764 |

FOREIGN PATENT DOCUMENTS

| 738028 | 7/1966 | Canada | 568/764 |
|---|---|---|---|
| 502080 | 3/1939 | United Kingdom | 568/764 |
| 634960 | 3/1950 | United Kingdom | |
| 1278582 | 6/1972 | United Kingdom | 528/152 |

*Primary Examiner*—Allan Lieberman
*Attorney, Agent, or Firm*—Daniel N. Hall; William H. Pittman; Raymond F. Keller

[57] ABSTRACT

Hydroxy aromatic compositions containing (a) a hydroxyl group bonded directly to a carbon of an aromatic nucleus, (b) a hydrocarbon-based substituent of at least about 50 aliphatic carbon atoms bonded directly to a carbon atom of an aromatic nucleus, (c) at least one methylol or lower hydrocarbyl substituted methylol substituent bonded directly to a carbon atom of an aromatic nucleus, and not having any alkylene linkages between carbon atoms of two aromatic nuclei are useful as additives for normally liquid fuels and lubricating oils. These hydroxy aromatic compositions are also useful as intermediates for preparing other additives for fuels and lubricants. Typical hydroxy aromatic compositions of the present invention are formed by reaction of formaldehyde with an alkenyl- or alkyl-substituted phenol wherein the alkyl or alkenyl substituent contains an average of about 50 carbon atoms.

15 Claims, No Drawings

HYDROCARBON-SUBSTITUTED METHYLOL PHENOLS

CROSS REFERENCE TO RELATED APPLICATIONS

This application is a continuation-in-part of U.S. Ser. No. 613,664 filed Sept. 15, 1975, now U.S. Pat. No. 4,053,428 which in turn is a continuation-in-part of U.S. Ser. No. 540,470 filed Jan. 13, 1975, now U.S. Pat. No. 3,980,569, which is a continuation-in-part of U.S. Ser. No. 451,644, filed Mar. 15, 1974, now abandoned.

BACKGROUND OF THE INVENTION

1. Field of the Invention

This invention relates to aromatic hydroxy compositions useful as additives for lubricants based on oils of lubricating viscosity and normally liquid fuels. More particularly, it relates to hydroxy aromatic compositions bearing a substituent of at least about 50 aliphatic carbon atoms and a methylol or substituted methylol group.

2. Prior Art

Hydrocarbon-substituted phenols containing methylol or substituted methylol groups are known in the art. See, for example, U.S. Pat. Nos. 3,306,938; 2,912,395; and 3,127,251 as well as British Patent Specification No. 634,960.

The reaction of alkyl phenols containing alkyl substituents of 400 to 5,000 molecular weight with formaldehyde has been reported to give bis(methylol-hydroxyalkylbenzyl) compounds which afford detergency/dispersancy properties to oils containing them; see, for example, U.S. Pat. No. 3,737,465. The '465 patent also points out that many resinous phenol formaldehyde condensation products of high molecular weight and complex structure are also known. Similar salt derivatives of both mono- and di(methylol)phenols are also known; see also U.S. Pat. No. 3,501,527.

3. General Background

Over the past several decades, a number of additive compositions have been developed which improve the performance characteristics of lubricants and normally liquid fuels to which they are added. Still, increasingly severe operating conditions as well as raw material shortages, environmental consciousness and increasing costs has spurred the search for and development of novel additives for fuels and lubricants. Therefore, it is an object of this invention to provide novel lubricant and fuel additives. A further object is to provide novel lubricants and fuels. A still further object is to provide novel concentrates of such additives.

It is also an object of this invention to provide novel intermediates for fuel and lubricant additives.

Other objects will be apparent to those skilled in the art upon review of the present specification.

SUMMARY OF THE INVENTION

The objects of this invention are achieved by providing compositions comprising at least one hydroxy aromatic compound having:

(a) at least one hydroxyl substituent bonded directly to a carbon atom of an aromatic moiety, Ar, (b) at least one hydrocarbon-based substituent of at least about 50 aliphatic carbon atoms bonded directly to a carbon atom of the aromatic moiety, Ar, and (c) at least one methylol or lower hydrocarbon-based substituted methylol substituent bonded directly to a carbon atom of the aromatic moiety Ar, said compound not having any alkylene linkages between carbon atoms of two aromatic nuclei. Lubricants based on oils of lubricating viscosity, normally liquid fuels and additive concentrates containing the above-described compositions are also within the scope of this invention.

DETAILED DESCRIPTION OF THE INVENTION

The aromatic moiety, Ar, can be a single ring nucleus such as a benzene ring, pyridine ring, thiophene ring, etc., or a polynuclear aromatic moiety. Such polynuclear moieties can be of the fused type (e.g., wherein two rings are fused at two points to another ring, such as found in naphthalene, anthracene, etc.) or they can be of the linked type, wherein individual aromatic rings (of either the mono- or fused polynuclear type) are linked through divalent bridging linkages. Such bridging linkages can be chosen from the group consisting of carbon-to-carbon single bonds; ether linkages (such as $-CH_2OCH_2-$); sulfide linkages (such as $-S-$); polysulfide linkages of 2 to 6 sulfur atoms (such as $-S_{2-6}-$); sulfinyl linkages (such as $-S(O)-$); sulfonyl linkages (such as $-S(O)_2-$); lower alkylene sulfur linkages (such as $-CH_2CH_2S-$); lower alkylene polysulfide linkages of 2 to 6 sulfur atoms (such as $-CH_2S_{2-6}-$); amino linkages (such as $-NH-$); polyamino linkages (such as $-(CH_2CH_2N)_{1-10}-$); and mixtures of such divalent bridging linkages. When Ar is a linked polynuclear aromatic moiety, generally there are not more than about 20 individual nuclei present and thus no more than 19 linkages. As stated above, the hydroxy aromatic compounds of this invention do not contain any alkylene linkages (e.g., methylene, $-CH_2-$) between aromatic rings. When Ar is polynuclear the hydroxyl substituents, aliphatic substituents, and methylol substituents can be bonded to different nuclei.

Generally Ar is a ring nucleus or a fused double ring nucleus which can be represented by the general formula Ar′ wherein Ar′ is a benzene, naphthalene, X-substituted benzene or X-substituted naphthalene nucleus, X being selected from the group consisting of lower alkyl substituents, lower alkoxy substituents, lower mercapto substituents, fluorine atoms, chlorine atoms and nitro substituents. There may be two or more X substituents per Ar′ and such X substituents may be the same or different. When such X substituents are present in Ar′ they are not present to such an extent as to prevent attachment of at least one $C_{50}+$ hydrocarbon substituent, at least one hydroxyl substituent and at least one methylol or substituted methylol substituent on Ar′. Usually, no more than two X substituents are present in Ar′. Typically, Ar′ is a benzene or naphthalene nucleus not having any X substituents.

Exemplary of Ar′ nuclei are: benzene, toluene, xylene, anisole, fluorobenzene, chlorobenzene, nitrobenzene, methoxyanisole, ethylbenzene, heptylmethylbenzene, methylmercaptobenzene nuclei. A benzene nucleus is preferred because of the ready availability of compounds providing such a nucleus.

As used in this specification, the term "lower" in conjunction with, for example, alkyl and alkoxy, refers to groups having 7 or less carbon atoms such as alkyl and alkoxy groups.

The hydroxy aromatic compounds of the present invention have at least one hydrocarbon-based substituent of at least about 50 aliphatic carbon atoms which can be conveniently represented by R. Generally R has less than about 300 carbon atoms and usually it has between about 70 and about 200 carbon atoms. Although R is aliphatic in nature it can contain small amounts of carbocyclic groups (e.g., cycloalkyl or aromatic), such as one group for every 20 noncyclic aliphatic carbons, which do not significantly alter its aliphatic character. Usually, however, R is purely aliphatic and contains only aliphatic carbon atoms.

As used herein, the term "hydrocarbon-based substituent" denotes a substituent having a carbon atom directly bonded to the remainder of the molecule and having predominantly hydrocarbyl character within the context of this invention. Such substituents include the following:

(1) Purely hydrocarbon substituents, that is aliphatic (e.g., alkyl or alkenyl) substituents containing only carbon and hydrogen.

(2) Substituted hydrocarbon substituents, that is, those containing non-hydrocarbon radicals which, in the context of this invention, do not alter the predominantly hydrocarbyl character of the substituent. Those skilled in the art will be aware of suitable radicals (e.g., halo, (especially chloro and fluoro), lower alkoxyl, lower alkyl mercapto, nitro, sulfoxy, etc. radicals). The main hydrocarbon chain can also contain a small number of hetero atoms such as oxygen or sulfur in the form of ether and sulfide linkages. In general, no more than about three radicals or hetero atoms, and usually no more than one, will be present for each 20 carbon atoms in the hydrocarbon-based substituent.

Generally, the hydrocarbon-based substituent, R, in the compositions of this invention are free from acetylenic unsaturation. Ethylenic unsaturation, when present, usually will be such that no more than one ethylenic linkage is present for every 10 carbon-to-carbon bonds in the substituent. The substituents, R, are usually purely hydrocarbon in nature and are typically saturated hydrocarbon.

Examples of the hydrocarbon-based substituents, R, are substituents derived from the homopolymerization or interpolymerization of olefins such as ethylene, propylene, 1-butene, 2-butene, isobutene, pentenes, hexenes, and similar monoolefins up to $C_{20}$. Usually $C_{2-10}$ 1-monoolefins are used. Substituents derived from polymers of ethylene, propylene, 1-butene and isobutene are preferred, especially those containing at least about 80 and usually not more than about 200 aliphatic carbon atoms. Typically, one to three, usually one or two such substituents are present. Usually at least one such substituent is in a para position with regard to the phenolic hydroxyl group. Often there is but one substituent para to the phenolic hydroxyl and the aromatic nucleus is a benzene nucleus. An exemplary class of such preferred polymers are those formed by Lewis Acid—catalyzed polymerization of olefin mixtures containing predominantly (i.e., greater than 50%) isobutene. Another preferred class of polymers is those which contain predominantly (i.e., greater than 50 mole %) isobutane repeat units, i.e.,

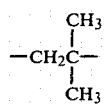

repeat units.

The production of olefin polymers and halogenated and hydrohalogenated analogs which serve as intermediates for such R substituents is well known to those skilled in the art; see, for example, the article entitled "Olefin-polymers-Higher Polyolefins" in Vol. 14, pages 309–313 of the below-mentioned Kirk-Othmer "Encyclopedia of Chemical Technology." These R substituents can be attached to the aromatic nuclei, Ar, by techniques discussed hereinbelow.

The hydroxy aromatic compounds of this invention also have at least one methylol or lower hydrocarbon-based substituted methylol substituent directly bonded to a carbon of the aromatic nucleus, Ar. The lower hydrocarbon-based substituents have up to seven carbon atoms and can be alkyl (e.g., methyl, ethyl, etc.), alkenyl (propenyl, etc.), aryl (e.g., phenyl, tolyl), and alkaryl (e.g., benzyl). They can be represented by "hyd" and the methylol substituents thus can be represented by —CH₂OH (methylol),

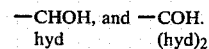

Usually the substituent is methylol itself or an alkyl-substituted methylol or phenyl-substituted methylol substituent, e.g.,

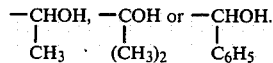

While the specific substituents of the hydroxy aromatic compounds of this invention (i.e., the hydroxyl substituent, hydrocarbon-based substituent, R, and the methylol substituent) can be attached to the aromatic nucleus, Ar, in any sequence of reactions, it is generally optimal to attach them in the order OH, R, methylol. This can be done, for example, when Ar is a benzene nucleus, by first alkylating a phenol and then reacting the alkylated product with an aldehyde or ketone or functional equivalents thereof.

The introduction of R substituents onto hydroxy aromatic compounds is usually affected by mixing an intermediate such as an olefin homopolymer, interpolymer or a halogenated analog thereof and, for example, a phenol at a temperature at about 10°–200° C. in the presence of a suitable catalyst such as aluminum trichloride, boron trifluoride, zinc chloride, or the like; see, for example, U.S. Pat. No. 3,368,972 which is hereby incorporated by reference for its disclosures in this regard. A substituent can also be introduced by other alkylation processes known to the art; see, for example, the article entitled "Alkylation of Phenols" in Kirk-Othmer "Encyclopedia of Chemical Technology", Second Edition, Vol. 1, pages 894–895, Interscience Publishers, a division of John Wiley & Sons, New York, 1963.

To be useful for the production of the hydroxy aromatic compounds of this invention, the intermediate thus produced must be a hydroxy aromatic intermediate having at least one hydrocarbon-based substituent of at least 50 aliphatic carbon atoms and, in addition, at least one unsubstituted aromatic ring carbon usually located in an alpha or gamma position to an aromatic carbon bearing a hydroxyl group. This unsubstituted aromatic ring carbon is necessary to provide a site for the subsequent attachment of the methylol or substituted methylol substituent. These intermediates can be represented by the formula $$(HO)_x Ar(H)_y(R)_z$$

wherein x, y and z are each at least one and their sum does not exceed the available valences of Ar.

The methylol or substituted methylol group can be introduced by reaction of the hydroxy aromatic intermediate with a hydrocarbon-based aldehyde or functional equivalent thereof. Suitable aldehydes include formaldehyde, benzaldehyde, acetaldehyde, butyraldehyde, hydroxy butyraldehyde, hexanals, etc.d "Functional equivalents" are materials (e.g., solutions, polymers, hydrates, etc.) which react as aldehydes under the conditions of the reaction and include such materials as paraformaldehyde, hexamethylenetetramine, paraldehyde, formalin and methylal. Should di-substituted methylol groups be desired, the aldehyde is replaced with an appropriate ketone, such as acetone, methyl ethyl ketone, acetophenone, benzophenone, and the like. Mixtures of aldehydes and/or ketones can also be used to produce compounds having mixtures of methylol groups.

Formaldehyde and functional equivalents are generally preferred, since they yield the preferred methylol groups. Introduction of the methylol groups usually takes place by reacting the hydroxy aromatic intermediate with an aldehyde, ketone or functional equivalent thereof in the presence or absence of an acidic or alkaline reagent. When the reaction takes place in the absence of such reagent, usually a portion of the mixture becomes acidic or alkaline by insitu degradation of the aldehyde or ketone; excess hydroxy aromatic intermediate can also fulfill this function.

Generally, however, the reaction of the aldehyde, ketone or functional equivalent thereof takes place in the presence of an alkaline reagent such as an alkali metal or alkaline earth metal oxide, hydroxide or lower alkoxide, at a temperature up to about 160° C. Other alkaline reagents which can be used include sodium carbonate, sodium bicarbonate, sodium acetate, sodium propionate, pyridine, and hydrocarbon-based amines such as methyl amine and aniline; naturally, mixtures of two or more bases can be used. Preferably, the reaction takes place in the temperature range of about 30° to about 125° C.; more usually, it is carried out between 70° and 100° C.

The relative proportions of hydroxy aromatic intermediates, and aldehyde, ketone or functional equivalent thereof are not critical. It is generally satisfactory to use 0.1–5 equivalents of aldehyde and about 0.05–10.0 equivalents of alkaline reagent per equivalent of hydroxy aromatic compound. As used herein, the term "equivalent" when applied to a hydroxy aromatic compound indicates the weight of such compound equal to the molecular weight thereof divided by the number of unsubstituted aromatic carbons bearing hydrogen atoms. As applied to the aldehyde, ketone or functional equivalent thereof, an "equivalent" is the weight required to produce one mole of monomeric aldehyde. An equivalents of alkaline reagent is that weight of reagent which when dissolved in one liter of solvent (e.g., water) will give a one normal solution. One equivalent of alkaline reagent will therefore neutralize, i.e., bring to pH7 a one normal solution of, for example, hydrochloric or sulfuric acid.

It is generally convenient to carry out the reaction of the hydroxy aromatic intermediate in the presence of a substantially inert, organic liquid diluent which may be volatile or non-volatile. This diluent may dissolve all the reactants, or it may not, but in any event, it does not substantially effect the course of the reaction under the prevailing conditions though, in certain cases, it may promote the speed of the reaction by increasing the contact of the reagents. Suitable diluents include hydrocarbons such as naphtha, textile spirits, benzene, toluene, xylene; mineral oils (which are among the preferred); synthetic oils (as described hereinbelow); alcohols, such as isopropanol, butanol, isobutanol, amyl alcohol, ethyl hexanols and the like; ethers, such as triethylene or diethylene glycol mono- or di-ethyl ether and the like, as well as mixtures of two or more of these.

The reactions of the hydroxy aromatic intermediate with aldehyde or ketone generally takes place in 0.5 to 8 hours, depending on such factors as the reaction temperature, amount and nature of alkaline catalyst used, etc. The control of such factors is well within the skill of the art and the effect of these factors is apparent. After the reaction has been completed to the desired extent, it can be substantially stopped by neutralization of the reaction mixture when an alkaline reagent is present. This neutralization can be effected with any suitable acidic material, typically a mineral acid or an organic acid or anhydride; an acidic gas such as carbon dioxide, hydrogen sulfide, sulfur dioxide and the like, can be used. Generally neutralization is accomplished with a carboxylic acid, especially a lower alkanoic carboxylic acid such as formic acid, acetic or propionic acid; mixtures of two or more acids can, of course, be used to accomplish the neutralization. The neutralization is carried out at a temperature of about 30° to 150° C. An amount of neutralizing agent sufficient to substantially neutralize the reaction mixture is used. Substantial neutralization means that the reaction mixture is brought to a pH ranging between 4.5 and 8.0. Usually the reaction mixture is brought to a minimum pH of about 6 or a maximum pH of about 7.5.

The reaction product, i.e., the hydroxy aromatic compositions of this invention, can be recovered from the reaction mixture by such techniques as filtration (for example, to remove the product of the neutralization of the alkaline reagent) followed by distillation, evaporation, etc. Such techniques are well known to those skilled in the art.

These compositions contain at least one compound which can be represented by the general formula

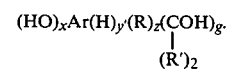

wherein x, z and g are each at least one; y' is 0 or at least one, the sum of x, y', z and g does not exceed the available valences of Ar; each R' is hydrogen or a "hyd" substituent as described above, and R is as described above. Often, however, it is not necessary to isolate the hydroxy aromatic compound formed from the reaction solvent, especially if it is to be blended in a fuel or lubricant or to be used as an intermediate for further reactions. In the latter case, the reagents for further reaction (such as those discussed hereinbelow) can be added directly to the product mixture; alternatively, the reaction mixture can be filtered to remove any solids present and the filtrate thus obtained used in further reactions.

When the reaction temperature is in the higher range, i.e., above about 100° C., substantial amounts of ether condensation products can be formed. It is believed that these condensates have the general formula

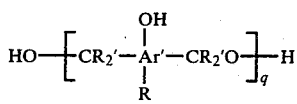

wherein q is a number ranging from 2 to about 10. These condensates thus contain alkylene ether linkages, i.e., —CR'$_2$O— linkages. Thus, for example, in the case of the reaction of a para alkyl phenol with formaldehyde, ether condensates are formed having the general formula

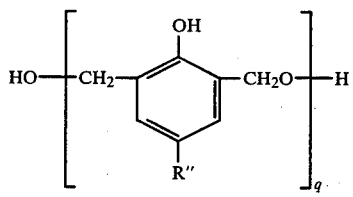

wherein q is a number ranging from 2 to about 10 and R" is an alkyl group of at least 50 carbon atoms. Typically R" has at least about 80 carbon atoms. It is possible that small amounts of such ether condensates accompany the predominantly largely uncondensed hydroxy aromatic compounds produced at lower temperatures.

If a strong acid, such as a mineral acid, is used for the neutralization, it is important to control the amount thereof present so as not to bring the reaction mixture to a lower pH than specified hereinabove. For example, at lower pH's, over-condensation occurs to form methylene-bridged phenols. Such methylene-bridged phenols are not within the scope of the present invention. The use, however, of carboxylic acids avoids this problem since they are of sufficiently low acidity they do not promote over-condensation and it is not necessary to regulate so closely the amount of carboxylic acid used.

The typical phenol or naphthol/formaldehyde-based hydroxy aromatic compounds of this invention have the general formula

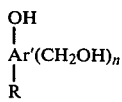

wherein Ar' is a benzene, naphthalene, X-substituted benzene or X-substituted naphthalene nucleus, n is 1 or 2, and R is a hydrocarbon-based substituent of at least about 50 aliphatic carbon atoms, and X is selected from the group consisting of lower alkyl groups, lower alkoxy groups, lower mercapto groups, fluorine atoms, chlorine atoms and nitro groups. An especially preferred class of hydroxy aromatic compounds are those made from phenols and have the general formula

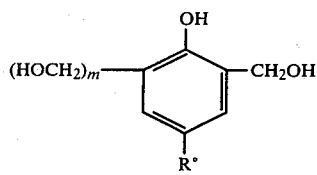

wherein R° is an alkyl substituent of about 50 to about 300 carbon atoms derived from polymerization or interpolymerization of at least one monoolefin of 2 to 10 carbon atoms, and m is 1 or 0. Typically, R° contains at least about 80 carbon atoms and is predominantly isobutene repeat units.

The following are specific illustrative examples of the hydroxy aromatic compounds of the present invention and include the best mode presently known. All parts and percentages in the examples and elsewhere herein are by weight unless it is expressly stated to the contrary. All temperatures are in degrees centigrade (°C.) unless expressly stated to the contrary. Molecular weights are determined by vapor phase osmometry (VPO) or gel permeation chromatography (GPC). The textile spirits used in these examples is an aliphatic petroleum naphtha with a boiling range of about 63°–79° at 760 torr.

EXAMPLE 1A

Polyisobutenyl chloride (4885 parts) having a viscosity at 99° of 1306 SUS and containing 4.7% chlorine is added to a mixture of 1700 parts phenol, 118 parts of a sulfuric acid-treated clay and 141 parts zinc chloride at 110°–155° during a 4-hour period. The mixture is then kept at 155°–185° for 3 hours before being filtered through diatomaceous earth. The filtrate is vacuum stripped to 165°/0.5 torr. The residue is again filtered through diatomaceous earth. The filtrate is a substituted phenol having an OH content of 1.88%.

EXAMPLE 1B

Sodium hydroxide (42 parts of a 20% aqueous sodium hydroxide solution) is added to a mixture of 453 parts of the substituted phenol described in Example 1A and 450 parts isopropanol at 30° over 0.5 hour. Textile spirits (60 parts) and 112 parts of a 37.7% formalin solution are added at 20° over a 0.8 hour period and the reaction mixture is held at 4°–25° for 92 hours. Additional textile spirits (50 parts), 50 parts isopropanol and acetic acid (58 parts of a 50% aqueous acetic acid solution) are added. The pH of the mixture is 5.5 (as determined by ASTM procedure D-974). The mixture is dried over 20 parts magnesium sulfate and then filtered through diatomaceous earth. The filtrate is vacuum stripped to 25°/10 torr. The residue is the desired methylol-substituted product having an OH content of 3.29%.

EXAMPLE 2A

Aluminum chloride (76 parts) is slowly added to a mixture of 4220 parts polyisobutenyl chloride having a number average molecular weight, Mn, of 1000 (VPO) and containing 4.2% chlorine, 1516 parts phenol, and 2500 parts toluene at 60°. The reaction mixture is kept at 95° under a below-the-surface nitrogen gas purge for 1.5 hours. Hydrochloric acid (50 parts of a 37.5% aqueous hydrochloric acid solution) is added at room temperature and the mixture stored for 1.5 hours. The mixture is washed five times with a total of 2500 parts water and then vacuum stripped to 215°/1 torr. The residue is filtered at 150° through diatomaceous earth to improve its clarity. The filtrate is a substituted phenol having an OH content of 1.39%, a Cl content of 0.46% and a $\overline{M}n$ of 898 (VPO).

EXAMPLE 2B

Paraformaldehyde (38 parts) is added to a mixture of 1399 parts of the substituted phenol described in Example 2A, 200 parts toluene, 50 parts water and 2 parts of a 37.5% aqueous hydrochloric acid solution at 50° and held for one hour. The mixture is then vacuum stripped to 150°/15 torr and the residue is filtered through diatomaceous earth. The filtrate is the desired product having an OH content of 1.60%, $\overline{M}n$ of 1688 (GPC) and a weight number average molecular weight, $\overline{M}w$, of 2934 (GPC).

EXAMPLE 3A

Boron trifluoride gas (3.8 parts) is introduced via a sparger underneath the surface into 168 parts phenol at 49°–53° during a 0.42 hour period. A solution (519 parts) containing 678 parts polyisobutene having an $\overline{M}n$ of 1600 (VPO) and 133 parts benzene is added at 54°–57° during a 1.7 hour period and held at 57° for 2.3 hours. A 26% aqueous ammonia solution (6.5 parts) is added to the reaction mixture at 56°–58° during a 1-hour period and then the mixture is kept at 69° for 0.67 hour. The mixture is filtered through diatomaceous earth and the filtrate is vacuum stripped to 228°/15 torr. The residue is a substituted phenol having an OH content of 0.91% and a $\overline{M}n$ of 1439 (VPO).

EXAMPLE 3B

Sodium hydroxide (352 parts of a 25% aqueous sodium hydroxide solution) is added to a mixture of 3740 parts of a substituted phenol prepared as described in Example b 3A, 1250 parts textile spirits and 2000 parts isopropanol at 34° C. Formaldehyde (480 parts of a 37.7% formalin solution) is added over a 0.75 hour period at 34°. The reaction mixture is held at 30°–34° for 114 hours. Acetic acid (150 parts of a commercially available glacial acetic acid) and 3663 parts diluent oil is added at 30°. The mixture is then vacuum stripped to 50°/30 torr. The residue is filtered through diatomaceous earth and the filtrate is a 49% oil solution of the desired product having an OH content of 1.33%.

EXAMPLE 4

Sodium hydroxide (842 parts of a 25% aqueous sodium hydroxide solution) is added to a mixture of 5200 parts of a substituted phenol, prepared as described in Example 3A except the polyisobutene used has a $\overline{M}n$ of 940 (VPO), 1200 parts toluene and 1200 parts isopropanol at 35°. Formaldehyde (600 parts of a 37.7% formalin solution) is added to the mixture of 35° during a 0.33 hour period and the mixture is kept at 35°–30° for a 15-hour period. Additional formaldehyde (400 parts of a 37.7% formalin solution) is added and the reaction mixture is held at 30° for a 20-hour period. Hydrochloric acid (416 parts of a commercially available 37.5% aqueous hydrochloric acid solution) is added. The pH of the mixture is 6. Benzene (2000 parts) and 1500 parts additional toluene are added and the mixture is azeotroped to 95° under a partial vacuum. Diluent oil (2000 parts) is added and the mixture is then vacuum stripped to 95°/30 torr. The residue is filtered through diatomaceous earth and the filtrate is a 30% oil solution of the desired product having an OH content of 1.69%.

EXAMPLE 5

Benzene (200 parts) is added to 1110 parts of the azeotroped to 95° under a partial vacuum mixture as described in Example 4 and the reaction temperature is raised to 160° and kept there for 3 hours. The mixture is then filtered through diatomaceous earth at 150° and the filtrate is vacuum stripped to 150°/10 torr. The residue is the desired product having an OH content of 1.73% and a Mn of 5252 (GPC) and a $\overline{M}w$ of 2171 (GPC).

EXAMPLE 6

Sodium hydroxide (8 parts of a 50% aqueous sodium hydroxide solution) and 145 parts paraformaldehyde are added to a mixture of 2240 parts of a substituted phenol prepared as described in Example 2A except the polyisobutene used has a $\overline{M}n$ of 940 (VPO), and 1271 parts diluent oil at 60° and the mixture kept at 80° for 22 hours. Acetic acid (6 parts of glacial acetic acid) is added and the mixture is held at 150° for 2 hours and then filtered through diatomaceous earth. The filtrate is a 35% oil solution of the desired product having an OH content of 1.10%.

EXAMPLE 7

Sodium hydroxide (32 parts of a 50% aqueous sodium hydroxide solution) and 290 parts paraformaldehyde are added to a mixture of 4480 parts of the substituted phenol used in Example 6 and 3099 parts diluent oil at 40°–50°; the mixture is kept at 80°–85° for a 14-hour period. Acetic acid (36 parts of glacial acetic acid) is added at 60°. The mixture is held at 110°–130° for a period of 12 hours and then is filtered through diatomaceous earth. The filtrate is a 40% oil solution of the desired product having an OH content of 1.05%.

EXAMPLE 8

Sodium hydroxide (8 parts of a 50% aqueous sodium hydroxide solution) and 145 parts paraformaldehyde are added to a mixture of 2080 parts of the substituted phenol described in Example 4 and 1400 parts diluent oil at 55° and the mixture is held at 70°–78° for a 7-hour period. Acetic acid (9 parts glacial acetic acid) is added at 60° and then the mixture is held at 130° for a 6-hour period. The residue is a 40% oil solution of the desired product having an OH content of 1.28% and a viscosity at 99° of 884 SUS.

The compositions of this invention are useful in and of themselves as anti-rust and anti-corrosion agents for fuels and lubricants. They are also useful as intermediates for the production of compositions that function in fuels and lubricants as detergents and dispersants for sludge formed in internal combustion engines.

The compositions of this invention can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, such as automobile and truck engines, two-cycle engines, marine and railroad diesel engines, and the like. They can also be used in gas engines, stationary power engines, turbines and the like. Automatic transmission fluids, transaxle lubricants, gear lubricants, metal-working lubricants, hydraulic fluids and other lubricating oil and grease compositions can also benefit from the incorporation therein of the compositions of the present invention.

Natural oils include animal oils and vegetable oils (e.g., castor oil, lard oil) as well as mineral lubricating oils such as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halosubstituted hydrocarbon oils such as polymerized and interpolymerized olefins (e.g., polybutylenes, polypropylenes, propylene-isobutylene copolymers, chlorinated polybutylenes, etc.); poly(1-hexenes), poly(1-octenes), poly(1-decenes), etc. and mixtures thereof; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$–$C_8$ fatty acid esters, or the $C_{13}$Oxo acid diester of tetraethylene glycol.

Another suitable class of synthetic lubricating oils comprises the esters of dicarboxylic acids (e.g., phthalic acid, succinic acid, alkyl succinic acids, alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methyl-hexyl)silicate, tetra-(p-tert-butylphenyl)silicate, hexyl-(4-methyl-2-pentoxy)-disiloxane, poly(methyl)siloxanes, poly(methylphenyl)siloxanes, etc.). Other synthetic lubricating oils include liquid esters of phosphorus-containing acids (e.g., tricresyl phosphate, trioctyl phosphate, diethyl ester of decane phosphonic acid, etc.), polymeric tetrahydrofurans and the like.

Unrefined, refined and rerefined oils, either natural or synthetic (as well as mixtures of two or more of any of these) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from primary distillation or ester oil obtained directly from an esterification process and used without further treatment would be an unrefined oil. Refined oils are similar to the unrefined oils except they have been further treated in one or more purification steps to improve one or more properties. Many such purification techniques are known to these of skill in the art such as solvent extraction, secondary distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

In general, about 0.05–20.0, preferably 0.1–10 parts (by weight) of a composition of this invention is dissolved or stably dispersed in 100 parts of oil to produce a satisfactory lubricant. The invention also contemplates the use of other additives in combination with the composition of this invention. Such additives include, for example, auxiliary detergents and dispersants of the ash-producing or ashless type, oxidation inhibiting agents, pour point depressing agents, extreme pressure agents, color stabilizers and anti-foam agents.

The fuel compositions of the present invention contain a major proportion of a normally liquid fuel, usually a hydrocarbonaceous petroleum distillate fuel such as motor gasoline as defined by ASTM Specification D-439-73 and diesel fuel or fuel oil as defined by ASTM Specification D-396. Normally liquid fuel compositions comprising nonhydrocarbonaceous materials such as alcohols, ethers, organo-nitro compounds and the like (e.g., methanol, ethanol, diethyl ether, methyl ethyl ether, nitromethane) are also within the scope of this invetion as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol, diesel fuel and ether, gasoline and nitromethane, etc. Particularly preferred is gasoline, that is, a mixture of hydrocarbons having an ASTM boiling point of 60° C. at the 10% distillation point to about 205° C. at the 90% distillation point.

Generally, these fuel compositions contain an amount of the compound of this invention sufficient to impart anti-oxidant and/or dispersant and detergent properties to the fuel; usually this amount is about 1 to about 10,000, preferably 4 to 1,000, parts by weight of the reaction product per million parts by weight of fuel. The preferred gasoline-based fuel compositions generally exhibit excellent engine oil sludge dispersancy and detergency properties. In addition, they resist oxidation.

The fuel compositions of this invention can contain, in addition to the compositions of this invention, other additives which are well known to those of skill in the art. These can include anti-knock agents such as tetraalkyl lead compounds, lead scavengers such as haloalkanes (e.g., ethylene dichloride and ethylene dibromide), deposit preventors or modifiers such as triaryl phosphates, dyes, cetane improvers, anti-oxidants such as 2,6-di-tertiarybutyl-4-methylphenol, rust inhibitors, such as alkylated succinic acids and anhydrides, bacteriostatic agents, gum inhibitors, metal deactivators, demulsifiers, upper cylinder lubricants, anti-icing agents and the like.

In certain preferred fuel compositions of the present invention, the afore-described compositions of this invention are combined with other ashless dispersants in gasoline. Such ashless dispersants are preferably esters of a mono- or polyol and a high molecular weight mono- or polycarboxylic acid acylating agent containing at least 30 carbon atoms in the acyl moiety. Such esters are well known to those of skill in the art. See, for example, French Pat. No. 1,396,645, British Pat. Nos. 981,850 and 1,055,337 and U.S. Pat. Nos. 3,255,108; 3,311,558; 3,331,776; 3,346,354; 3,522,179; 3,579,450; 3,542,680; 3,381,022; 3,639,242; 3,697,428; 3,708,522; and British Patent Specification No. 1,306,529. These patents are expressly incorporated herein by reference for their disclosure of suitable esters and methods for their preparation. Generally, the weight ratio of the compositions of this invention to the aforesaid ashless dispersants is about 0.1 to about 10.0; preferably about 1 to about 10 parts of composition of this invention to 1 part ashless dispersant.

In still another embodiment of this invention, the compositions are combined with Mannich condensation products formed from substituted phenols, aldehydes, polyamines, and amino pyridines to make lubricants and/or fuel additives. Such condensation products are described in U.S. Pat. Nos. 3,649,659; 3,558,743; 3,539,633; 3,704,308; and 3,725,277.

The compositions of this invention can be added directly to the fuel or lubricating oil to form the fuel and lubricant compositions of this invention or they can be diluted with at least one substantially inert, normally liquid organic solvent/diluent such as mineral oil, xylene, or a normally liquid fuel as described above, to form an additive concentrate which is then added to the fuel or lubricating oil in sufficient amounts to form the inventive fuel and lubricant composition described herein. These concentrates generally contain about 20 to about 90 percent of the composition of this invention and can contain in addition any of the above-described conventional additives, particularly the afore-described ashless dispersants in the aforesaid proportions. The remainder of the concentrate is the solvent/diluent.

As well as serving as additives in and of themselves, the compounds of this invention can be used as intermediates to form compositions which are also useful as additives in the afore-described fuels and lubricants.

For example, the methylol-substitued phenols of this invention can be condensed with amines and polyamines having at least one >NH group to form useful engine sludge dispersant/detergent compositions. Such condensation can be conveniently carried out by heating the phenol/amine mixture in the presence of benzene or toluene while removing the by-product water by azeotropic distillation. Further details of such condensations can be found in French Pat. No. 75 07709, filed Mar. 12, 1975, which is hereby incorporated by reference for its relevant disclosures in this regard.

What is claimed is:
1. A lubricant and liquid fuel additive or intermediate for such additives selected from the group consisting of (I) hydroxy aromatic compounds having:
   (a) at least one hydroxyl substituent bonded directly to a carbon atom of an aromatic moiety, Ar,
   (b) at least one hydrocarbon-based substituent of at least about 50 and up to about 300 aliphatic carbon atoms bonded directly to a carbon atom of the aromatic moiety, Ar, and
   (c) at least one methylol or lower hydrocarbon-based substituted methylol substituent bonded directly to a carbon atom of the aromatic moiety, Ar, said compound containing no alkylene linkages between carbon atoms of two aromatic nuclei, (II) ether condensates of said hydroxy aromatic compounds and mixtures of (I) and (II).

2. An additive or intermediate as claimed in claim 1 wherein the hydrocarbon-based substituent has no more than about 300 aliphatic carbon atoms.

3. An additive or intermediate as claimed in claim 1 wherein the substituent (c) is a methylol substituent, $CH_2OH$.

4. An additive or intermediate as claimed in claim 2 wherein the hydrocarbon-based substituent (b) is derived from homopolymerization or interpolymerization of at least one 1-monoolefin of 2 to 10 carbon atoms.

5. An additive or intermediate as claimed in claim 4 wherein said monoolefin contains predominantly isobutene and the substituent (c) is at least one methylol substituent.

6. An additive or intermediate as claimed in claim 1 wherein the hydroxy aromatic compounds (I) are represented by the general formula

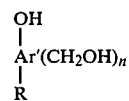

wherein Ar' is a benzene, naphthalene, X-substituted benzene or X-substituted naphthalene nucleus, n is 1 or 2, and R is a hydrocarbon-based substituent of at least about 50 aliphatic carbon atoms, X being selected from the group consisting of lower alkyl substituents, lower alkoxy substituents, lower mercapto substituents, fluorine atoms, chlorine atoms and nitro substituents.

7. An additive or intermediate as claimed in claim 6 wherein R has up to about 300 carbon atoms and is derived from homopolymerization or interpolymerization of at least one 1-monoolefin of 2 to 10 carbon atoms.

8. An additive or intermediate as claimed in claim 7 wherein the hydroxy aromatic compounds (I) are represented by the general formula

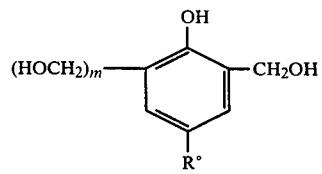

wherein R° is an alkyl substituent of about 50 to about 300 carbon atoms derived from polymerization or interpolymerization of at least one monoolefin of 2 to 10 carbon atoms, and m is 1 or 0.

9. An additive or intermediate as claimed in claim 1 made by reacting at a temperature up to about 160° C. at least one hydroxy aromatic compound having a hydrocarbon-based substituent of at least 50 and up to about 300 aliphatic carbon atoms, and at least one unsubstituted aromatic ring carbon, with formaldehyde or a lower hydrocarbon substituted formaldehyde or functional equivalent thereof in the presence of an alkaline reagent.

10. An additive or intermediate as claimed in claim 9 wherein formaldehyde or a functional equivalent thereof is used and the alkaline reagent is selected from the group consisting of alkali metal and alkaline earth metal oxides, hydroxides and lower alkoxides.

11. An additive or intermediate as claimed in claim 10 wherein the hydroxy aromatic compound is phenol, naphthol, X-substituted phenol or X-substituted naphthol and X is selected from the group consisting of lower alkyl substituents, lower alkoxy substituents, lower alkyl mercapto substituents, fluorine atoms, chlorine atoms and nitro substituents.

12. An additive or intermediate as claimed in claim 8 wherein R° is an alkyl group of at least about 80 carbons containing predominantly isobutane repeat units.

13. A lubricant and liquid fuel additive or intermediate for such additives selected from the group consisting of (I) hydroxy aromatic compounds which can be represented by the general formula

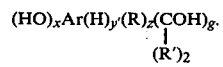

wherein x, z and g are each at least one; y' is 0 or at least one, the sum of x, y', z and g does not exceed the available valences of Ar; each R' is hydrogen or a hydrocarbon-based substituent of up to seven carbon atoms and each R is a hydrocarbon-based substituent of at least about 50 and up to about 300 aliphatic carbon atoms, (II) ether condensates of said hydroxy aromatic compounds and mixtures of (I) and (II).

14. An additive or intermediate as claimed in claim 13 wherein the hydroxy aromatic compounds (I) are represented by the formula

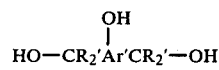

and the ether condensate (II) is represented by the formula

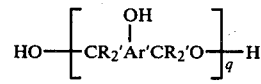

wherein Ar is a benzene, naphthalene, X-substituted benzene or X-substituted naphthalene nucleus, X being selected from the group consisting of lower alkyl substituents, lower alkoxy substituents, lower mercapto substituents, fluorine atoms, chlorine atoms and nitro substituents, and q is a number ranging from 2 to about 10.

15. An additive or intermediate as claimed in claim 14 wherein the hydroxy aromatic compounds (I) are para alkyl phenol-formaldehyde reaction products which are represented by the formula

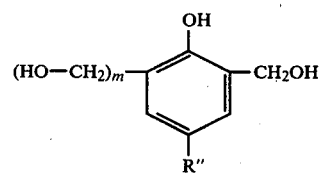

wherein m is 1 or zero and R" is an alkyl group of at least 50 and up to about 300 carbon atoms and the ether condensate (II) is represented by the formula

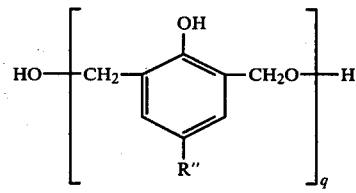

* * * * *

UNITED STATES PATENT AND TRADEMARK OFFICE
CERTIFICATE OF CORRECTION

PATENT NO. : 4,273,891
DATED : June 16, 1981
INVENTOR(S) : John F. Pindar; Jerome M. Cohen; Charles P. Bryant It is certified that error appears in the above-identified patent and that said Letters Patent are hereby corrected as shown below:

Column 7, line 13, "$CR_2'$" should be --$CR'_2$--, each occurrence.

Claim 14, line 4, in the formula, "$CR_2'$" should be --$CR'_2$--, each occurrence.

Claim 14, line 11, in the formula, "$CR_2'$" should be --$CR'_2$--, each occurrence.

Signed and Sealed this

Eighth Day of September 1981

[SEAL]

Attest:

Attesting Officer

GERALD J. MOSSINGHOFF

Commissioner of Patents and Trademarks